US011375946B2

(12) United States Patent
Petit et al.

(10) Patent No.: US 11,375,946 B2
(45) Date of Patent: Jul. 5, 2022

(54) UV DEVICE FOR SMARTPHONE-BASED EVALUATION OF SKIN CONDITIONS

(71) Applicants: GALDERMA RESEARCH AND DEVELOPMENT, Biot (FR); Laurent Petit, Peymeinade (FR); Laurent Chantalat, New York, NY (US)

(72) Inventors: Laurent Petit, Peymeinade (FR); Laurent Chantalat, New York, NY (US)

(73) Assignee: GALDERMA RESEARCH AND DEVELOPMENT, Biot (FR)

( * ) Notice: Subject to any disclaimer, the term of this patent is extended or adjusted under 35 U.S.C. 154(b) by 651 days.

(21) Appl. No.: 16/327,253

(22) PCT Filed: Aug. 17, 2017

(86) PCT No.: PCT/US2017/047293
§ 371 (c)(1),
(2) Date: Feb. 21, 2019

(87) PCT Pub. No.: WO2018/039024
PCT Pub. Date: Mar. 1, 2018

(65) Prior Publication Data
US 2019/0183416 A1    Jun. 20, 2019

Related U.S. Application Data

(60) Provisional application No. 62/377,904, filed on Aug. 22, 2016.

(51) Int. Cl.
*A61B 5/00* (2006.01)

(52) U.S. Cl.
CPC ............ *A61B 5/4833* (2013.01); *A61B 5/004* (2013.01); *A61B 5/0071* (2013.01); *A61B 5/441* (2013.01); *A61B 5/444* (2013.01); *A61B 5/4842* (2013.01); *A61B 5/6898* (2013.01)

(58) Field of Classification Search
CPC ....... A61B 5/004; A61B 5/0071; A61B 5/441; A61B 5/444; A61B 5/4833; A61B 5/4842; A61B 5/6898
See application file for complete search history.

(56) References Cited

U.S. PATENT DOCUMENTS

| | | |
|---|---|---|
| 2003/0063801 A1 | 4/2003 | Rubinstenn et al. |
| 2003/0138249 A1 | 7/2003 | Merola et al. |
| 2011/0117025 A1 | 5/2011 | Dacosta et al. |
| 2017/0202504 A1* | 7/2017 | Suzuki ................. A61B 5/1032 |

FOREIGN PATENT DOCUMENTS

| | | |
|---|---|---|
| CN | 104939806 | 9/2015 |
| JP | 2011-521237 A | 7/2011 |
| WO | WO-2015/159732 | 10/2015 |

OTHER PUBLICATIONS

Lucchina et al., "Fluorescence photography in the evaluation of acne", Journal of the American Academy of Dermatol, vol. 35, No. 1, Jul. 1, 1996, pp. 58.
Stamatas et al., "Modern Technology for Imaging and Evaluation of Acne Lesions", in "Pathogenesis and Treatment of Acne and Rosacea", Jan. 1, 2014.
Vasefi et al., "Vanishing point: a smartphone application that classifies acne lesions and estimates prognosis", Proceedings Optical Diagnostics of Living Cells II, vol. 9711, Mar. 14, 2016.
International Search Report issued in PCT/US2017/047293, dated Nov. 14, 2017.
Written Opinion of the International Searching Authority issued in PCT/US2017/047293, dated Nov. 14, 2017.

* cited by examiner

*Primary Examiner* — Mark D Remaly
(74) *Attorney, Agent, or Firm* — Sunit Talapatra; Foley & Lardner LLP

(57) ABSTRACT

A method for evaluating skin conditions on a skin area of a user using an ultraviolet light device that can connect to a mobile device and a user input is disclosed. The method for evaluating skin conditions includes the steps of illuminating the skin area of the user with the ultraviolet light device operated by the mobile device, capturing an image of the illuminated skin area with an image capture device, processing the image with a processing program to determine the level of fluorescence on the skin area, and mapping progress of treatment of the skin condition based on the processed image compared to a control image.

12 Claims, No Drawings

UV DEVICE FOR SMARTPHONE-BASED EVALUATION OF SKIN CONDITIONS

CROSS-REFERENCE TO RELATED APPLICATIONS

This application is the National Phase of International Patent Application No. PCT/US2017/047293, filed Aug. 17, 2017, published on Feb. 8, 2018 as WO 2018/039024 A1, which claims priority to U.S. Provisional Application No. 62/377,904, filed Aug. 22, 2016. The contents of these applications are herein incorporated by reference in their entirety.

BACKGROUND OF THE INVENTION

Many prescription and over-the-counter drugs have significant patient compliance issues which reduce the effectiveness of the drug treatments. In some cases, poor patient compliance results from the patient being unable to detect improvements in their condition, even when improvement is occurring. Some conditions do not show immediate and significant visual improvement, even though the condition is improving in ways that are not visually apparent to the patient. In other cases, patients simply have poor "customer engagement" with the drug treatment.

A blacklight (black light), also referred to as a UV light, Wood's lamp, or ultraviolet light, is a lamp that emits long-wave (UV) ultraviolet light and only a small amount of visible light. In the medical field, such a light source is referred to as a Wood's lamp, named after Robert Williams Wood. A Wood's lamp is helpful in diagnosing bacterial infections, including *Propionibacterium acnes*, also referred to as "*P. acnes*," which is a bacterium involved in acne. This bacterium exhibits an orange-type glow under a Wood's lamp. More specifically, acne fluoresces orange-red under a Wood's lamp due to *Propionibacteria* in hair follicles. Hereafter, the UV light/lamp is referred to as a "blacklight."

As described in U.S. Patent Application No. 2003/0063801 (Rubinstenn et al.), features of a facial image may be extracted by illuminating a portion of the subject's skin with a Wood's lamp. The Wood's lamp may help identify an amount of acne-causing bacteria on the portion of the subject's skin by making visible on the subject's skin residues, such as porphyrine, excreted by the bacteria. Porphyrine is thus a surrogate marker for for *P. acnes*. An image of the illuminated residue may then be captured for image processing.

DESCRIPTION OF PREFERRED EMBODIMENTS

Mobile devices, and particularly, mobile device applications such as mobile phone application software ("apps") are proven tools for increasing customer engagement. The present invention employs such an app as a companion device for use by patients who are undergoing a drug treatment for a skin condition or who are using a skin care product. The mobile device may be any type of handheld computing device having an operating system (OS), and capable of running apps. Examples of such a mobile device include, but are not limited to, a smartphone, tablet computer and PDA. The OS is typically Apple's iOS® or Google's Android®, but may be any suitable mobile OS. The mobile device includes a controller or processor, such as a general purpose processor, a digital signal processor, or other programmable logic device, programmed to execute the logic or algorithm of the app.

Current advances in LED technology allow for the production of LEDs which produce UV, which allows for the development of an efficient, cheap, miniaturized LED wood lamp for use with mobile devices including smartphones and tablets.

Embodiments of the invention relate to the use of an LED UV device connected to a mobile device for the evaluation of skin conditions. In particular, the UV device may include but is not limited to a UV LED flash light with a UV wavelength between 270 and 440 nm. The UV device may connect to the mobile phone via any suitable means including but not limited to physical connection or Bluetooth.

Skin conditions may include but are not limited to increase in pigmentation (ex. melasma, postinflammatory pigmentation); loss of pigmentation (ex. Vitiligo, ash-leaf macules in tuberous sclerosis, and hypomelanosis of Ito); pityriasis versicolor; malassezia folliculitis; tinea capitis; head lice; scabies; erythrasma; *Pseudomonas* (wound infection); acne (*Propoionibacteria*); poryphia; presence of porphyrins; application of salicylic acid (ex. application of chemical peel); photodamage; application of sunscreen; acne; and actinic keratosis.

In one general aspect, embodiments of the invention relate to the use of a UV device for the evaluation of skin conditions comprising a processing program (mobile phone application software) and a user interface device (mobile device), wherein the processing program is capable of processing a captured image, identifying skin fluorescence produced by the UV device on the skin of a user in the captured image, and mapping skin parameters and trends in relation to the user based on comparisons between a captured image or images and a control image or images.

According to an embodiment of the invention, the captured image is preferably a two-dimensional image. The captured image may comprise multiple images, for example superimposed to create one two-dimensional image. For example, a facial captured image can comprise a left facial side image, a right facial side image, and a frontal facial image, superimposed to create one two-dimensional facial image. In certain embodiments, the facial captured images can comprise a left facial side image, a right facial side image, and a frontal facial image superimposed to create one three-dimensional facial image. The captured image can be acquired by any photographing image capture device, preferably a camera phone or a tablet camera. The captured image can be acquired by a camera phone comprising dual-camera technology.

I. Acne-Related Skin Condition

In one preferred embodiment, an app is used for patients undergoing acne treatment. Acne treatment is particularly prone to poor patient compliance and customer engagement. One type of acne treatment involves applying a topical product to the acne, such as a product that uses benzoyl peroxide (e.g., Proactive® or Benzac AC® or Epiduo®.

In one preferred embodiment, the app is used in conjunction with a blacklight, as follows:

1. The app is opened on the user's mobile device. ("Patient" and "user" are used herein interchangeably.)
2. Using the app, the user takes one or more photographs (photos) of the area where acne is present (typically, the face) while the area is illuminated by the blacklight.

3. The app provides an algorithm that computes a severity index of the acne based on the porphyrin presence at the surface of the skin based on the fluorescence level detected at the surface of the skin. In some embodiments, to compute the severity index, the app compares the amount of porphyrin present at the surface of the skin imaged by the user (e.g., the density of detected porphyrin in the one or more photographs of the area in which acne is present) to a control image stored in the memory of the mobile device. The memory may be transitory memory and/or non-transitory memory. For example, non-transitory memory may be implemented as RAM, ROM, flash, ferromagnetic, phase-change memory, and other non-transitory memory technologies.

In some embodiments, the control image may be a stock image having a predetermined amount of porphyrin illuminated by the blacklight. The predetermined amount of porphyrin may be an amount that represents a low (or zero) severity index of acne. The app may then compare the one or more photographs taken by the user to the control image and calculate a difference in the amount of porphyrin detected in the recently taken images to the amount of porphyrin present in the control image. The app may then assign a severity index based on the calculated difference.

In certain embodiments, the app also tracks serial photos and shows the overall progress during treatment in any suitable visual format, such as graphically. For example, the app may compare the one or more photographs taken by the user to an initial photograph taken by the user before the start (or at the start) of treatment and stored in the memory of the mobile device, which may serve as a control image. The app may then calculate a difference in the amount of porphyrin detected in the recently taken images to the amount of porphyrin detected in the initial image. The app may then graphically display the difference to the user to indicate the overall progress of the treatment. The graphical display may be in the form of, for example, a numerical value (e.g., percent difference, severity index difference), a trend line, or an image comparison (e.g., side-by-side image comparison of the taken image or images to the initial image or images, graphically morphing of the initial image showing the initial amount of porphyrin detected to the taken image showing the present amount of porphyrin detected). In additional embodiments, the app may graphically display overall progress based on images taken during the treatment process to further illustrate trends in progress.

In another embodiment, the blacklight may be a UV synchronized flash light for mobile devices. The blacklight may be optimized for fluorescence associated with the skin condition. In a preferred embodiment, the blacklight is optimized for fluorescence associated with *P. acnes*. Optimization of the blacklight may include but is not limited to flash wavelength, flash intensity (number of LEDs), and flash duration.

The UV flash light can be directly connected to the mobile device through the headphone port, the USB port, the lightening port or by Bluetooth. The UV flash light may include its own rechargeable battery.

In another embodiment, the blacklight is a filter mounted or applied over the internal LED light of the mobile device that is normally used as a flash for the camera and as a flashlight. It is well-known in the art to mount camera filters over the camera lens of a smartphone. A similar filter may be mounted over the LED light of the mobile device. However, since the algorithm in the app is calibrated for specific color ranges, it is preferable to use a commercially produced light filter to minimize variations in color intensity and shades. In this embodiment wherein the blacklight is a filter applied over the internal LED light of the mobile device, step 1 involves simply turning on the flashlight app of the mobile device after the filter is mounted or attached.

The algorithm in the app analyzes the photo of the skin, particularly, the porphyrin level that is visible due to its fluorescence, and then counts, measures and estimates the level of *P. acnes*, and provides a quantitative output to the user via the acne severity index. The app may provide further information, such as number of lesions, trends in the acne severity index, the user's history, and advice on how to improve usage of the acne medication including product application tips. The app may further include other parameters for user input including symptoms such as inflammation and oiliness level, and potential triggering factors including but not limited to food, alcohol, tobacco use. The app may also provide parameters including but not limited to pollution and UV index. The app may provide the user the opportunity to compare acne severity index scores within an acne community.

By more actively engaging the user/patient in the acne treatment via the app, product usage and effectiveness will likely improve, particularly if the severity index shows a declining trend, thereby confirming to the patient that the acne treatment is working, even if it is not immediately noticeable. Likewise, if the acne treatment is not working, the patient may be informed via the app of alternative treatment methods or other lifestyle tips that may improve the acne condition.

II. Sunscreen Application

In another preferred embodiment of the present invention, a UV flashlight (blacklight) used in combination with a mobile device, is used to verify the correct application of sunscreen. The following steps are employed in this embodiment:

1. The app is opened on the user's mobile device.
2. Using the app, the user takes one or more photographs (photos) of the area(s) where the sunscreen was applied or intended to be applied, while the area is illuminated by the blacklight.
3. The app provides an algorithm that computes the effectiveness of the sunscreen application. A quantitative evaluation of the sunscreen application is provided to the user for each photo. In certain embodiments, a control image having an optimal amount of sunscreen application (e.g., an optimal overall density of sunscreen detected) is stored in the memory of the mobile device. The app compares the detected amount of sunscreen present in the one or more photos taken by the user to the control image to determine the effectiveness of the sunscreen application. The app may then graphically display an indication of the effectiveness of the sunscreen application. For example, the app may graphically display a scaling factor or index level (e.g., relative scale of 1 to 10) on the effectiveness of the sunscreen application. In additional embodiments, areas of poor application are highlighted to the user so that additional sunscreen can be applied to the areas of poor application. For example, the app may graphically display the effectiveness of the sunscreen application by providing relative coloring on the photos taken by the user (e.g., red indicating areas of poor application and green indicating areas of optimal or appropriate application).

When a photo of skin is taken with UV light, the darker the skin in the photo, the less UV light is being absorbed by it, which means the skin is better protected. Thus, the darker the image, the better. Likewise, white patches show areas of skin where a lot of UV light is getting through, indicating poor application of sunscreen. These principles are incorporated into the algorithm of the app to provide the quantitative evaluation.

III. Photodamage

Photodamage refers to the structural and functional deterioration of sun-exposed skin, specifically damage to skin and/or DNA caused by exposure to ultraviolet radiation. In another preferred embodiment of the present invention, a UV flashlight (blacklight) used in combination with a mobile device, is used to identify potential photodamage. The following steps are employed in this embodiment:

1. The app is opened on the user's mobile device.
2. Using the app, the user takes one or more photographs (photos) of the area(s) where the potential photodamage is being investigated, while the area is illuminated by the blacklight.
3. The app provides an algorithm that computes a quantitative measure of photodamage using the images in the photos. The quantitative measure is communicated to the user within the app, along with recommended products that can be used and/or lifestyle actions that can be taken to reduce the amount of future photodamage. In certain embodiments, a control image having a low or zero level of photodamage is stored in the memory of the mobile device. The app compares the detected amount of photodamage present in the one or more photos taken by the user to the control image and provides a quantitative measure of the determined difference to the user. The app may graphically display an indication of the photodamage present on the user. For example, the app may graphically display a scaling factor or index level (e.g., relative scale of 1 to 10) of the severity of the user's photodamage. In other embodiments, the control image or images are previous images taken by the user and stored in the memory of the mobile device. The app may then compare the detected amount of photodamage present in the one or more photos taken by the user to the previous images. The app may graphically display an indication of the progress of severity of photodamage present on the user and/or provide an indication in the reduction of progress of photodamage over time.

IV. Actinic Keratoses (AK) Lesions

Actinic keratoses (AK), also called solar keratoses, are scaly, crusty growths (lesions) caused by damage from the sun's ultraviolet (UV) rays. They typically appear on sun-exposed areas such as the face, bald scalp, lips, and the back of the hands, and are often elevated, rough in texture, and resemble warts.

In another preferred embodiment of the present invention, a UV flashlight (blacklight) used in combination with a mobile device, is used to identify AK. The following steps are employed in this embodiment:

1. The app is opened on the user's mobile device.
2. Using the app, the user takes one or more photographs (photos) of the area(s) where AK is being investigated, while the area is illuminated by the blacklight
3. The app provides an algorithm that computes a quantitative measure of AK using the images in the photos. The quantitative measure is communicated to the user within the app, along with recommended products that can be used and/or lifestyle actions that can be taken to reduce the severity of existing AK lesions and/or to reduce the amount of future AK lesions. In certain embodiments, a control image having a low or zero level of AK lesions is stored in the memory of the mobile device. The app compares the detected amount of AK lesions present in the one or more photos taken by the user to the control image and provides a quantitative measure of the determined difference to the user. The app may graphically display an indication of the AK lesions present on the user. For example, the app may graphically display a scaling factor or index level (e.g., relative scale of 1 to 10) of the severity of the user's AK. In other embodiments, the control image or images are previous images taken by the user and stored in the memory of the mobile device. The app may then compare the detected amount of AK lesions present in the one or more photos taken by the user to the previous images. The app may graphically display an indication of the progress of severity of AK present on the user and/or provide an indication in the reduction of progress of AK over time.

Endogenous photosensitizer protoporphyrin IX (PpIX, also referred to herein as "PP9") may be a surrogate condition for AK lesions. Fluorescence emitted by methyl ester of ALA (MAL)-induced PP9 may be useful in providing a fluorescence diagnosis of cutaneous lesions. This permits the detection of otherwise occult areas of abnormal skin. Tumor margins can also be delineated with the use of the blacklight. In one preferred embodiment, these principles are incorporated into the algorithm of the app to provide the quantitative measure.

We claim:

1. A method for evaluating a skin condition on a skin area of a user using a UV LED device configured to connect to a mobile device and responsive to user input, the method comprising:
   a. illuminating the skin area of the user with the UV device, which is configured to be operable using the mobile device;
   b. capturing an image of the illuminated skin area with an image capture device;
   c. processing the image with a mobile application, which the mobile device is configured to store, to determine a level of fluorescence on the skin area; and
   d. evaluating the skin area following the processing, and comparing the processed image to a control image, and
   e. mapping progress of treatment of the skin condition based comparison of on the processed image to the control image,
   wherein capturing the image comprises capturing multiple images using the image capture device, and
   wherein the processing includes creating a two-dimensional image from the multiple images, the two-dimensional image comprising a left facial side image, a right facial side image, and a frontal facial image which are superimposed on each other.

2. The method according to claim 1, wherein the skin condition is acne.

3. The method according to claim 2, wherein the level of fluorescence produced by porphyrin on the skin area of the user is indicative of the presence of *Propionibacterium acnes*.

4. The method of claim 1, wherein mapping of progress of treatment includes calculation of an acne severity index for the user.

5. The method of claim 3, further comprising:
   calculating a difference in an amount of the porphyrin in a first image and in a second image, the second image being captured by the image capture device after the first image.

6. The method of claim 1, further comprising:
disposing a filter over an LED light of the mobile device, the filter serving as a blacklight.

7. The method of claim 1, wherein the skin condition is one selected from the group consisting of an increase in pigmentation, a loss of pigmentation, pityriasis versicolor, malassezia folliculitis, tinea capitis, head lice, scabies, erythrasma, *Pseudomonas,* acne, poryphia, presence of porphyrins, application of salicylic acid, photodamage, application of sunscreen, and actinic keratosis.

8. The method of claim 1, further comprising:
illuminating the skin area with a blacklight, wherein capturing the images comprises capturing one or more photographs, when the skin area is illuminated with the blacklight, of the skin area, in which sunscreen was applied or intended to be applied; and
determining the effectiveness of sunscreen application by comparing a detected amount of sunscreen present in the one or more photographs to the control image.

9. The method of claim 1, wherein the control image indicates an optimal overall density of sunscreen and is stored in a memory of the mobile device.

10. The method of claim 9, wherein:
the program is configured to indicate areas of poor application of sunscreen and of appropriate application of sunscreen, and
determining the effectiveness of sunscreen application includes a quantitative evaluation of the image based on absorption of UV light.

11. The method of claim 1, further comprising:
determining the level of fluorescence on the skin area to evaluate actinic keratoses,
wherein the fluorescence is emitted by methyl ester of ALA(MAL)-induced endogenous photosensitizer protoporphyrin IX.

12. The method of claim 1, further comprising:
illuminating the skin area with a blacklight, wherein capturing the images comprises capturing one or more photographs, when the skin area is illuminated with the blacklight, of the skin area; and
determining an extent of photodamage by comparing a detected amount of photodamage present in the one or more photographs to the control image.

* * * * *

UNITED STATES PATENT AND TRADEMARK OFFICE
CERTIFICATE OF CORRECTION

| | |
|---|---|
| PATENT NO. | : 11,375,946 B2 |
| APPLICATION NO. | : 16/327253 |
| DATED | : July 5, 2022 |
| INVENTOR(S) | : Laurent Petit and Laurent Chantalat |

It is certified that error appears in the above-identified patent and that said Letters Patent is hereby corrected as shown below:

On the Title Page

The Applicant information should read as follows:
(71) Applicant: GALDERMA RESEARCH AND DEVELOPMENT, Biot (FR)

Signed and Sealed this
Eighteenth Day of October, 2022

Katherine Kelly Vidal
*Director of the United States Patent and Trademark Office*